United States Patent
Kamat et al.

(10) Patent No.: US 11,650,157 B2
(45) Date of Patent: May 16, 2023

(54) SYSTEM FOR EXTENDING DYNAMIC RANGE AND CONTRAST OF A VIDEO UNDER FLUORESCENCE IMAGING

(71) Applicant: IRILLIC PVT LTD, Karnataka (IN)

(72) Inventors: Saish Kamat, Bangalore (IN); Navaneeth Mohanan, Bangalore (IN); Anant Chilkunda, Bangalore (IN); Viswanath Buravalla, Bangalore (IN); Sandeep Jaipurkar, Chennai (IN); Beera Devaiah Vijaya, Bangalore (IN)

( * ) Notice: Subject to any disclaimer, the term of this patent is extended or adjusted under 35 U.S.C. 154(b) by 714 days.

(21) Appl. No.: 16/605,472

(22) PCT Filed: Apr. 13, 2018

(86) PCT No.: PCT/IN2018/050212
§ 371 (c)(1),
(2) Date: Oct. 15, 2019

(87) PCT Pub. No.: WO2018/193465
PCT Pub. Date: Oct. 25, 2018

(65) Prior Publication Data
US 2020/0046225 A1 Feb. 13, 2020

(30) Foreign Application Priority Data
Apr. 20, 2017 (IN) .............................. 201741014037

(51) Int. Cl.
*G06K 9/00* (2022.01)
*G01N 21/64* (2006.01)
(Continued)

(52) U.S. Cl.
CPC ... *G01N 21/6456* (2013.01); *A61B 1/000095* (2022.02); *A61B 1/046* (2022.02);
(Continued)

(58) Field of Classification Search
CPC .......... A61B 1/00006; A61B 1/000095; A61B 1/00186; A61B 1/043; A61B 1/046;
(Continued)

(56) References Cited

U.S. PATENT DOCUMENTS

2015/0182118 A1* 7/2015 Bradbury ................ A61P 17/00
600/431
2016/0278621 A1 9/2016 Igarashi
(Continued)

FOREIGN PATENT DOCUMENTS

JP 2016137008 A 8/2016
WO 2015145814 A1 10/2015

*Primary Examiner* — Tom Y Lu

(57) ABSTRACT

The present invention provides a system for extension of dynamic range and contrast of a video capture under fluorescence imaging conditions using a single detector. For this purpose, the system (100) comprises of a light engine (107) which sequentially switches between a high-intensity fluorescence excitation light mode (107A), a low-intensity fluorescence excitation light mode (107B) and NIR reflectance light (107C). Correspondingly, a detector (103) captures three data streams—High Intensity Fluorescence Data (105A), Low Intensity Fluorescence Data (105B) and NIR Reflectance Data (105D). A scene processing unit (105) then processes the three data streams and generate two additional data streams—a Wide Dynamic Range Fluorescence Data Stream (105C) and an Enhanced Vascular Index Data Stream (105E). The system also uses a Selective Visualization Unit (106) to allow the user to visualize any of five data streams.

6 Claims, 3 Drawing Sheets

(51) Int. Cl.
  *A61B 5/00* (2006.01)
  *G06T 5/00* (2006.01)
  *G06T 5/50* (2006.01)
  *A61B 1/00* (2006.01)
  *A61B 1/04* (2006.01)
  *A61B 1/06* (2006.01)

(52) U.S. Cl.
  CPC .......... *A61B 1/0655* (2022.02); *A61B 5/0033* (2013.01); *A61B 5/0071* (2013.01); *A61B 5/7225* (2013.01); *A61B 5/7228* (2013.01); *G06T 5/007* (2013.01); *G06T 5/50* (2013.01); *G06T 2207/10064* (2013.01); *G06T 2207/20224* (2013.01)

(58) Field of Classification Search
  CPC ... A61B 1/0638; A61B 1/0646; A61B 1/0655; A61B 5/0033; A61B 5/0071; A61B 5/7225; A61B 5/7228; G01N 21/359; G01N 21/6456; G06T 2207/10064; G06T 2207/20224; G06T 5/007; G06T 5/50
  See application file for complete search history.

(56) References Cited

U.S. PATENT DOCUMENTS

| | | | |
|---|---|---|---|
| 2017/0017069 A1* | 1/2017 | Siegel | G01J 3/2823 |
| 2017/0176336 A1* | 6/2017 | Dimitriadis | G01J 3/32 |
| 2017/0251932 A1 | 9/2017 | Kaku | |

* cited by examiner

SYSTEM FOR EXTENDING DYNAMIC RANGE AND CONTRAST OF A VIDEO UNDER FLUORESCENCE IMAGING

PRIORITY CLAIM

This application claims priority from the provisional application numbered 201741014037 filed with Indian Patent Office, Chennai on 20 Apr. 2017 entitled "A System for Extending dynamic range and contrast of a video under fluorescence imaging", the entirety of which is expressly incorporated herein by reference.

PREAMBLE TO THE DESCRIPTION

The following specification particularly describes the invention and the manner in which it is to be performed.

DESCRIPTION OF THE INVENTION

Technical Field of the Invention

The present invention relates to the field of fluorescence imaging systems where dynamic range and contrast of an image or video captured under fluorescence imaging conditions is extended using a single detector using multi-frame, multi-intensity fluorescence combined with near infrared reflectance data.

BACKGROUND OF THE INVENTION

Most existing fluorescence imaging systems comprise of a single detector and capture only fluorescence data. However, doctors operating on a patient are more used to seeing organ tissues illuminated using the visible spectrum. With the absence of a familiar visible light image, doctors find it difficult to interpret just the fluorescence data. Some fluorescence imaging systems employ multiple detectors to simultaneously record both fluorescence and visible image which allows the doctor to switch between the fluorescence imaging feed and the familiar visible imaging feed. However, this multi detector is typically bulky, costly and difficult to miniaturize making their adaptation in use of laparoscopic and endoscopic application more challenging. Moreover, a multi detector approach employs complex optics to capture the both fluorescence data and reflectance data in the same optical plane. This results in higher optical losses sacrificing the sensitivity of the imaging system. Some fluorescence imaging systems have used a single detector to capture both fluorescence and NIR (Nearly Infrared) reflectance data. In one approach, this is achieved by interleaving fluorescence and NIR reflectance data in between the scan lines of the detector thereby sacrificing on detector resolution. In another approach, this is achieved by pixel level interpolation of fluorescence and NIR reflectance data using a RGB-NIR bayer pattern. This leads to sacrifice in detector resolution for accommodation of both fluorescence by the subject and NIR reflectance off the subject.

These are examples from a plethora of fluorescence imaging techniques in medical imaging.

One of the challenges of fluorescence imaging systems is the inability to continuously capture fluorescence data with large difference in concentrations of fluorescence. In such scenarios, the detector is able to either capture the data from the strongly fluorescing elements by sacrificing on the data from the weakly fluorescing elements or vice-versa. This is due to limited dynamic range of most detectors. Some fluorescence imaging systems have employed traditional HDR (High Dynamic Range) imaging techniques to capture such data. The HDR technique involves capturing data at multiple exposures and then combining them to product one image. However, multiple exposures mean longer exposure times and longer exposure time increases the dark noise captured along with the data from the weakly fluorescing tissues.

Some Fluorescence Imaging Systems have employed Laser Diode based light source to excite the fluorophore. However, this approach does not allow for illumination of the human tissues for extended duration of time due to patient safety considerations. The present invention solves this problem by employing the use of an LED based light source which is safe of long exposure to skin tissues.

One of the applications of the fluorescence imaging systems is the visualization of vascular tissues like arteries, veins and capillaries. However, due to the scattering effects of non-vascular tissues like fat, there's poor contrast between the vascular tissues and non-vascular tissues.

Hence, there exists a need of a system for extending the dynamic range and contrast of the subject under fluorescence conditions using a single detector.

SUMMARY OF THE INVENTION

The present invention overcomes the drawback in the prior art and provides a system for extending dynamic range and contrast of an image or video under fluorescence.

The present invention provides a three-step process. In the first step, the system captures three data streams namely, High intensity fluorescence data, Low intensity fluorescence data and Reflectance data sequentially frame by frame using a single high frame rate detector without sacrificing on the detector image resolution. The High Intensity Fluorescence Data is generated by illuminating the subject stained with the fluorophore (such as Indocyanine Green Dye) using an LED based Variable Excitation Light Source tuned for emitting a high intensity excitation light. The Low Intensity Fluorescence Data is generated by illuminating the subject stained with the fluorophore using the same LED based Variable Excitation Light Source tuned for low intensity excitation light. Lastly the NIR Reflectance Data is generated by illuminating the subject using a NIR Reflectance Light Source. The LED based variable excitation light source is suitably chosen to allow for long imaging sessions. In the second step, the imaging system combines the High Intensity Fluorescence Data and the Low Intensity Fluorescence Data to generate a Wide Dynamic Range Fluorescence Data. This Wide Dynamic Range Fluorescence Data captures both strongly fluorescing elements and weakly fluorescing elements without sacrificing one or the other thus extending the dynamic range of the fluorescence imaging system. In the third step, the Wide Dynamic Range Fluorescence Data is combined with the NIR Reflectance Data to generate the Enhanced Vascular Index Data. The Enhanced Vascular Index Data boosts the contrast of the vascular tissues with respect to the non-vascular tissues.

In a preferred embodiment of the invention, the system comprising a trigger generator which is used to generate Pulse Width Modulation (PWM) signals and transmit PWM signals to a light engine. The light engine further comprises a variable excitation light source and a near infrared reflectance (NIR) light source. Moreover, the system comprises an excitation filter or plurality of excitation filter used to transmit wavelengths of the light to the subject and receive at least one of high intensity fluorescence light, low intensity fluorescence light and NIR reflectance light as inputs. Furthermore, the system comprises of emission filter or plurality of emission filter which is used to receive a light signal of wavelength from the subject.

In a preferred embodiment of the invention, the system comprises a detector which is used to detect data and capture one complete plurality of image frame of received data. The system further comprises a scene processing unit used to read trigger signal from the detector and generate high intensity fluorescence data, low intensity fluorescence data, wide dynamic range florescence data, NIR reflectance data and enhanced vascular index data. Furthermore, the system also comprises a selective visualization unit configured to visualize an image or a video feed on a standard display using five data streams available from scene processing unit.

Further, the advantage of the present invention is that enhancing the dynamic range and contrast of a video or image under fluorescence imaging condition.

BRIEF DESCRIPTION OF THE DRAWINGS

The foregoing and other features of embodiments will become more apparent from the following detailed description of embodiments when read in conjunction with the accompanying drawings. In the drawings, like reference numerals refer to like elements.

DETAILED DESCRIPTION OF THE INVENTION

Reference will now be made in detail to the description of the present subject matter, one or more examples of which are shown in figures. Each example is provided to explain the subject matter and not a limitation. Various changes and modifications obvious to one skilled in the art to which the invention pertains are deemed to be within the spirit, scope and contemplation of the invention.

The term 'Dynamic Range' refers to the dynamic range of a video or image. It mainly refers to the range which an imaging sensor can successfully capture the lightest and darkest areas of a scene without losing detail.

The term 'Fluorescence Imaging' used herein represents a visualization of fluorophores as labels for body structures or tissues or cells.

The term 'Multi Exposure' used herein refers to the superimposition of two or more exposures to create a single image which is more prevalent in HDR fluorescence imaging technique.

The present invention overcomes the drawback of prior art by providing a system that extends the dynamic range and contrast of a video or image under fluorescence imaging conditions. For this purpose, the system of the present invention involves capturing of fluorescence at two intensities of excitation light. The system uses the low intensity excitation light for capturing strongly fluorescing tissues and high intensity excitation light for capturing weakly fluorescing tissues. The two frames obtained are then merged to generate a single frame that covers the wide dynamic range of a scene. This helps in capturing tissues with large differences in fluorescence concentrations without adding any dark noise to the image which is a major drawback in the prior art.

Figure 1:
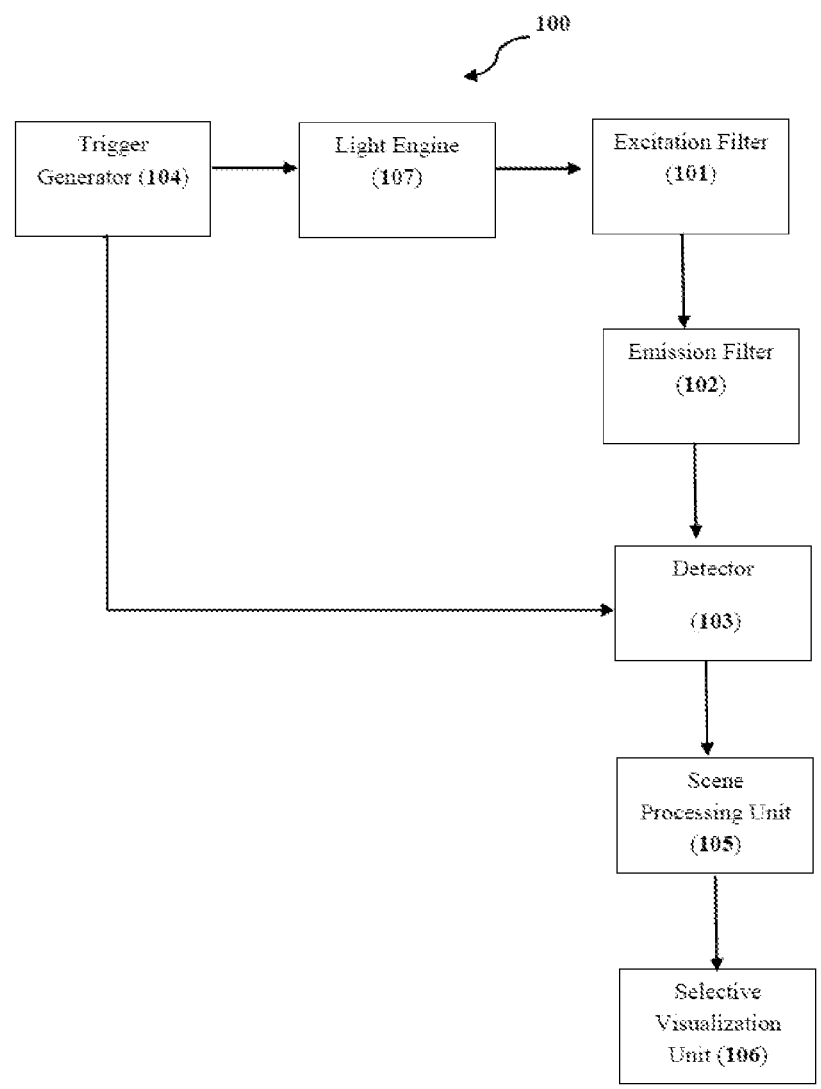
FIG. 1 illustrates a system for obtaining fluorescence and NIR reflectance data streams by using IR (Infrared) excitation light of different intensities of different wavelengths in accordance to one or more embodiment of the present invention.

FIG. 1 illustrates a system for obtaining fluorescence and non-fluorescence data streams by using IR excitation light of different intensities of different wavelengths in accordance to one or more embodiment of the present invention.

The system (100) of the present invention mainly comprises of a trigger generator (104), a light engine (107), a plurality of detector (103), a scene processing unit (105) and a selective visualization unit (106). The use of a single detector (103) in the present invention allows for miniaturization of the system as compared to the multi detector systems used in the prior art making its use in laparoscopic and endoscopic systems more amenable. The trigger generator (104) which is a part of the present invention is used to generate a PWM (Phase-Width Modulation) signal with a frequency of 3 times the imaging system's (100) output data rate. For example—if a 50 Hz output data rate is required, then the frequency of PWM signal to make this possible will be 150 Hz. In one embodiment of the present invention, the trigger generator (104) passes a PWM signal having frequency of 90 hertz which is suitably chosen to generate 30 Hz output data rate.

In accordance to one embodiment of the present invention, the trigger generator (104), which generates a PWM signal, transmits signal to the light engine (107) to switch the light source and triggers the detector (103) to capture one complete image frame. The light engine (107) consists of a variable intensity fluorescence excitation light source (108) and one broadband non-fluorescence NIR reflectance light source (109). The light engine (107) switches between one high intensity fluorescence excitation light mode (107A), one low intensity fluorescence excitation light mode (107B) and the NIR reflectance light (107C). The light sources may be arranged as a ring around the detector (103) to ensure uniform illumination of the subject (110). In a preferred embodiment, the wavelength of the fluorescence excitation light source (108) may be 760 nm+/−20 nm or 770 nm+/−20 nm or 780 nm+/−20 nm or whichever is the excitation wavelength of the fluorophore of choice and the wavelength of the NIR reflectance light source (109) may be 890 nm or any broad wavelength between 800-900 nm depending on the fluorophore of choice. The wavelength of the NIR reflectance light source (109) is chosen such that it does not excite the fluorophore but gets significantly absorbed by the vascular tissues in the body. The NIR reflectance light source (109) can be generated from a xenon lamp with an appropriate filter or an incandescent lamp with appropriate filter or an LED or LASER (Light Amplification by Stimulated Emission of Radiation) or any pulsed light source with appropriate filters.

In accordance to one or more embodiments of the present invention, the detector (103) used in the present invention is any CCD (Charge Coupled Device) or CMOS (Complementary Metal Oxide Semiconductor) or a combination of a CCD/CMOS and an Image Intensifier capture system or any imaging sensor. The trigger signal (104A) in the form of PWM signal generated by trigger generator (104) may also be generated from detector's (103) VSYNC (Vertical Synchronization) signal if supported by the detector (103). The receiving of trigger signal (104A) and capturing of one frame per trigger signal (104A) by high frame rate detector (103) from the trigger generator (104) results in interpolation at a frame level of complete high-resolution frames of High Intensity Fluorescence Data (105A), Low Intensity Fluorescence Data (105B) and NIR Reflectance Data (105D). In the NIR Reflectance Data (105D), the vascular tissues can be discriminated by hypo intensities in the images.

In accordance to one embodiment of the present invention, the system (100) comprises of a scene processing module (105) which generates an additional stream of wide dynamic range fluorescence data (105C). The wide dynamic range fluorescence data (105C) is generated by combining the High Intensity Fluorescence data (105A) and Low Intensity Fluorescence data (105B) from the detector output. The use of multiple intensities by the fluorescence light sources (108) ensures that fluorescence data from both strongly fluorescing tissues and weakly fluorescing tissues gets captured within the useful dynamic range of the imaging sensor. The present invention involves the use of variable intensity of light source instead of variable exposure due to which less dark noise is captured along with the weakly fluorescing tissues. In the Wide Dynamic Range Fluorescence Data (105C), the vascular tissues can be discriminated by hyper intensities in the images.

In accordance to one of the embodiments of the present invention, the scene processing module (105) optionally combines the Wide Dynamic Range Fluorescence Data with the NIR Reflectance Data (105D) to generate an Enhanced Vascular Index Data (105E). The Enhanced Vascular Index Data (105E) boosts the contrast ratio between the vascular tissues and non-vascular tissues.

In accordance to one of the embodiments of the present invention, the Enhanced Vascular Index Data (105E) can be generated by subtracting the NIR Reflectance Data (NIRFD) (105D) from the Wide Dynamic Range Fluorescence Data (WDRFD) (105C). Enhanced Vascular Index Data (105E)= (WDRFD−NIRFD).

In accordance to one of the embodiments of the present invention, the Enhanced Vascular Index Data can be generated by subtracting and normalizing the NIRFD (105D) from the WDRFD (105C). Enhanced Vascular Index Data (105E)=(WDRFD−NIRFD)/(WDRFD+NIRFD).

The Scene Processing Module (105) reads raw data in the form of trigger signal (104A) from the detector (103) and generates five data streams—i) High Intensity Fluorescence Data (105A), ii) Low Intensity Fluorescence Data (105B), iii) Wide Dynamic Range Fluorescence Data (105C), iv) NIR Reflectance Data (105D) and v) Enhanced Vascular Index Data (105E).

The Selective Visualization Unit (106) allows the user to input which stream he wishes to visualize from the five data streams made available by scene processing module (105) as a standard image or video feed on a standard display.

Figure 2:
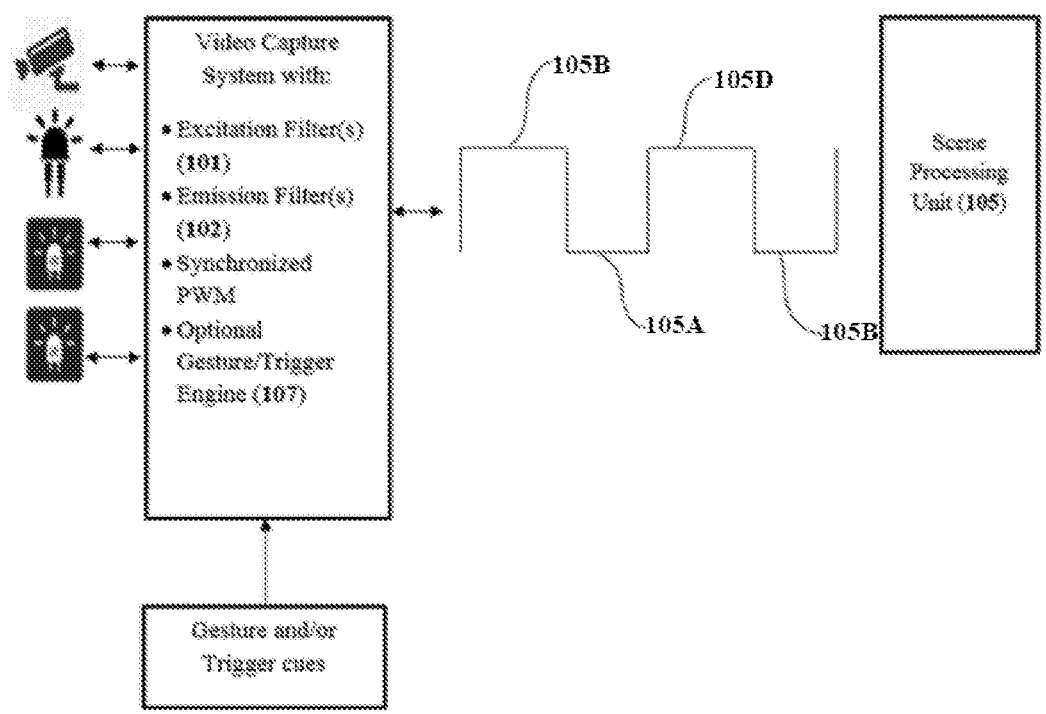
FIG. 2 illustrates a system for extracting fluorescence and NIR reflectance data by image processing system utilizing low and high intensities of IR excitation light of different wavelengths through an image or video capture system in accordance to one embodiment of the present invention.

FIG. 2 illustrates a system for extracting fluorescence and NIR Reflectance data by image processing system utilizing low and high intensities of fluorescence excitation light and NIR reflectance light through an image or video capture system in accordance to one embodiment of the present invention. The system for extracting fluorescence and NIR reflectance data by image processing system involves analyzing of low intensity fluorescence, high intensity fluorescence and NIR reflectance data.

Figure 3:
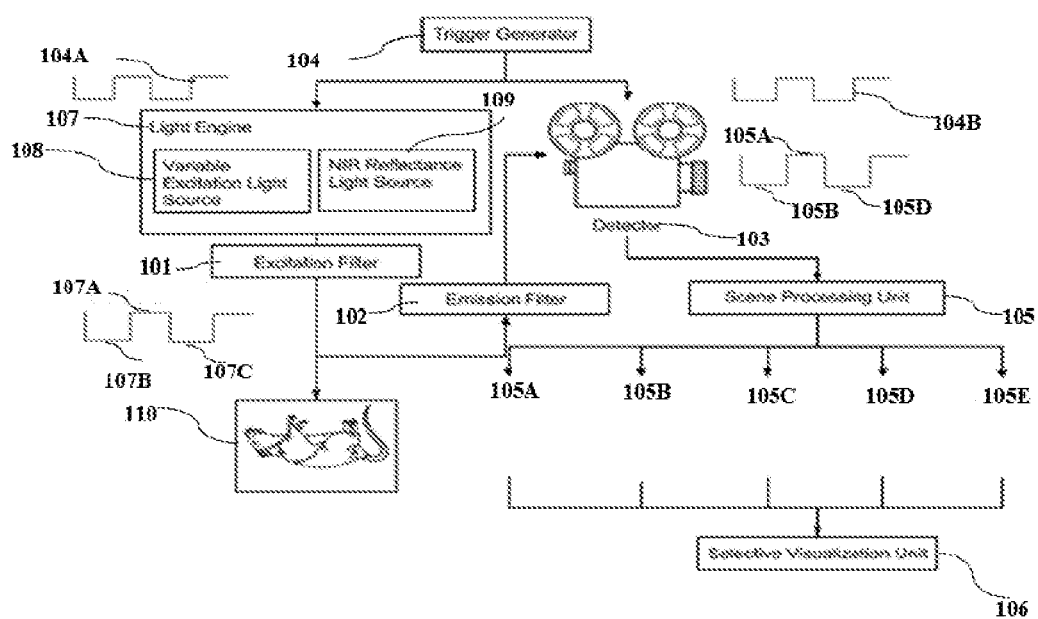
FIG. 3 illustrates a system for enhancing the dynamic range and contrast of a video or image under fluorescence imaging conditions as well as obtaining fluorescence and NIR reflectance image data frames using different light intensities of different wavelengths in accordance to one embodiment of the present invention.

FIG. 3 illustrates a system for enhancing the dynamic range and contrast of a video or image under fluorescence imaging conditions as well as obtaining fluorescence and NIR reflectance image data frames using different light intensities of different wavelengths in accordance to one embodiment of the present invention. Enhancement of dynamic range and contrast of an image or video captured of a scene is achieved by using dynamic excitation light sources for different intensities and adjustment of video or image is done using a single imaging sensor. Low intensity of IR light is used for obtaining low fluorescence data and high intensity of IR light is used for obtaining high fluorescence data.

Thus, the system (100) of the present invention extends the dynamic range of an image or video captured of a scene using variable intensities of light sources instead of variable exposure which leads to lowering of the dark noise captured in the weakly fluorescing tissues. The present invention also boosts the contrast of vascular tissues such as arteries and veins with respect to the non-vascular tissues such as fat tissues by generating enhanced vascular index.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A system for generating wide dynamic range fluorescence data and enhanced vascular Index data, the system comprising:
   a) a trigger generator (104) configured to generate Pulse Width Modulation (PWM) signals and transmit the PWM signals to a light engine (107), wherein the trigger generator (104) provides a plurality of trigger signals (104B) to {a} one or more detectors (103), wherein the trigger generator (104) provides a plurality of trigger signals (104A) to the light engine (107);
   b) the light engine (107) configured to provide different intensity of Infrared (IR) light of different wavelength, wherein the light engine (107) includes one or more variable excitation light source (108) and one and more near infrared reflectance (NIR) light sources (109);
   c) a plurality of excitation filters (101) configured to transmit wavelengths of the light to a subject (110), wherein the plurality of excitation filters (101) receives at least one of high intensity fluorescence light (107A), low intensity fluorescence light (107B) and NIR reflectance light (107C) as inputs;
   d) a plurality of emission filters (102) configured to receive a light signal of wavelength from the subject (110);
   e) the one or more detectors (103) configured to detect data from at least one of high intensity fluorescence data (105A), low intensity fluorescence data (105B) and NIR reflectance data (105C), wherein the one or more detectors (103) capture one or more image frame of received data, wherein the one or more detectors (103) is connected to the plurality of emission filters (102) to receive fluorescence light emitted by the subject (110);
   f) a scene processing unit (105) configured to read the plurality of trigger signals (104A) from the one or more detectors (103) and generate five data streams including the high intensity fluorescence data (105A), the low intensity fluorescence data (105B), wide dynamic range florescence data (105C), the NIR reflectance data (105D) and the enhanced vascular index data (105E), g) a selective visualization unit (106) configured to visualize an image or video feed on a standard display, wherein the selective visualization unit (106) visualizes the five data streams available from the scene processing unit (105), wherein the selective visualization unit (106) allows a user to input least one of the five data streams to visualize;

wherein the scene processing unit (105) combines a Wide Dynamic Range Fluorescence Data (WDRFD) with the NIR Reflectance Data (NIRFD) (105D) to generate the Enhanced Vascular Index Data (105E), wherein the Enhanced Vascular Index Data (105E) boosts a contrast ratio between vascular tissues and non-vascular tissues; and wherein the Enhanced Vascular Index Data (105E) is generated by at least one of: subtracting the NIR Reflectance Data (NIRFD) (105D) from the Wide Dynamic Range Fluorescence Data (WDRFD), subtracting and normalizing the NIRFD (105D) from the WDRFD, and mathematical combination of the NIRFD (105D) from the WDRFD.

2. The system of claim 1, wherein the trigger generator (104) generates the PWM signals with a frequency at least three times an imaging system (100).

3. The system of claim 1, wherein the one or more variable excitation light sources (108) provides the high intensity fluorescence light (107A) and the low intensity florescence light (107B), wherein the NIR reflectance light sources (109) provide the NIR reflectance light (107C).

4. The system of claim 3, wherein the one or more variable excitation light sources (108) is tuned for emitting the high intensity excitation light (107A) and the low intensity excitation light (107B).

5. The system of claim 4, wherein the low intensity excitation light (107B) is used for capturing strongly fluorescing tissues, wherein the high intensity excitation light (107A) is used for capturing weakly fluorescing tissues.

6. The system of claim 1, wherein the scene processing unit (105) generates an additional stream of wide dynamic range fluorescence data (105C), wherein the wide dynamic range fluorescence data (105C) is generated by combining the High Intensity Fluorescence data (105A) and Low Intensity Fluorescence data (105B) from an output of the one or more detectors (103).

* * * * *